(12) United States Patent
Martinez-Conde et al.

(10) Patent No.: US 7,857,452 B2
(45) Date of Patent: Dec. 28, 2010

(54) EYE MOVEMENTS AS A WAY TO DETERMINE FOCI OF COVERT ATTENTION

(75) Inventors: Susana Martinez-Conde, Anthem, AZ (US); Stephen L. Macknik, Anthem, AZ (US); Jorge Otero-Millan, Phoenix, AZ (US)

(73) Assignee: Catholic Healthcare West, Phoenix, AZ (US)

( * ) Notice: Subject to any disclaimer, the term of this patent is extended or adjusted under 35 U.S.C. 154(b) by 90 days.

(21) Appl. No.: 12/199,625

(22) Filed: Aug. 27, 2008

(65) Prior Publication Data
US 2010/0039617 A1    Feb. 18, 2010

Related U.S. Application Data

(60) Provisional application No. 60/968,238, filed on Aug. 27, 2007.

(51) Int. Cl.
*A61B 3/00* (2006.01)
(52) U.S. Cl. .................. 351/246; 351/209; 351/237; 356/3.14
(58) Field of Classification Search .................. 351/246
See application file for complete search history.

(56) References Cited

U.S. PATENT DOCUMENTS

| | | | | |
|---|---|---|---|---|
| 4,456,347 | A * | 6/1984 | Stahly | 351/158 |
| 4,889,422 | A * | 12/1989 | Pavlidis | 351/210 |
| 6,496,594 | B1 | 12/2002 | Prokoski et al. | |
| 7,309,125 | B2 | 12/2007 | Pugach et al. | |
| 7,549,743 | B2 | 6/2009 | Huxlin et al. | |
| 2003/0091215 | A1 * | 5/2003 | Lauper et al. | 382/117 |
| 2005/0108092 | A1 * | 5/2005 | Campbell et al. | 705/14 |
| 2007/0066916 | A1 * | 3/2007 | Lemos | 600/558 |
| 2007/0273832 | A1 * | 11/2007 | Weinblatt | 351/210 |
| 2008/0255949 | A1 * | 10/2008 | Genco et al. | 705/14 |
| 2008/0309880 | A1 | 12/2008 | Fisher et al. | |
| 2009/0012419 | A1 * | 1/2009 | McKee | 600/558 |

FOREIGN PATENT DOCUMENTS

WO   WO 2009/059167   5/2009

OTHER PUBLICATIONS

Saccades and Microsaccades During Visual Fixation, Exploration and Search: Foundation for a Common Saccadic Generator, Otero-Milan, et al. Journal of Vision (2008) 1-15.

(Continued)

*Primary Examiner*—Jessica T Stultz
(74) *Attorney, Agent, or Firm*—Husch Blackwell LLP Welsh & Katz

(57) ABSTRACT

A method and apparatus are provided for identifying the covert foci of attention of a person when viewing an image or series of images. The method includes the steps of presenting the person with an image having a plurality of visual elements, measuring eye movements of the subject with respect to those images, and based upon the measured eye movements triangulating and determining the level of covert attentional interest that the person has in the various visual elements.

42 Claims, 9 Drawing Sheets

OTHER PUBLICATIONS

Microsaccades Counteract Visual Fading During Fixation, Martinez-Conde, et al., Neuron 49, 297-305, Jan. 19, 2006 Elsevier, Inc.

The Role of Fixational Eye Movements in Visual Perception, Martinez-Conde, et al., Nature Reviews/Neuroscience Nature Publishing Group, vol. 5, Mar. 2004, 229-240.

A Simple After Image Method Demonstrating the Involuntary Multi-Directional Eye Movements During Fixation, F.J. Verheijen, Laboratory of Comparative Physiology, University of Utrecht, The Netherlands, 4 pages.

Microsaccadic Eye Movements and Firing of Single Cells in the Striate Cortex of Macaque Monkeys, Martinez-Conde, et al., Nature Neuroscience, vol. 3, No. 3, Mar. 2000, pp. 251-258.

Flicker Distorts Visual Space Constancy, Macknik, et al., Vision Res., vol. 31, No. 12, pp. 2057-2064 (in revised form Apr. 24, 1991).

Vision with a Stabilized Retinal Image, R.W. Ditchburn, et al., Jul. 5, 1952, Nature, vol. 170, pp. 36-37.

Microsaccades as an Overt Measure of Covert Attention Shifts, Ziad M. Hafed, et al., Vision Research 42 (2002) 2533-2545, Elsevier Science Ltd., (2002).

The Extraordinarily Rapid Disappearance of Entoptic Images, David Coppola, et al., Proc. Natl. Acad. Sci, USA, vol. 93, pp. 8001-8004, Jul. 1996 Neurobiology.

The Function of Bursts of Spikes During Visual Fixation in the Awake Primate Lateral Geniculate Nucleus and Primary Visual Cortex, Martinez-Conde, et al., PNAS, vol. 99, No. 21, Oct. 15, 2002, pp. 13920-13925.

Microsaccades Uncover the Orientation of Covert Attention, Ralf Engbert, et al., Vision Research, 43 (2003) pp. 1035-1045.

PCT Search Report and Written Opinion (Dec. 11, 2009) 11 pages.

\* cited by examiner

US 7,857,452 B2

EYE MOVEMENTS AS A WAY TO DETERMINE FOCI OF COVERT ATTENTION

FIELD OF THE INVENTION

The field of the invention relates to evaluating the attentional focus particularly to using eye movements as a way to determine foci of covert attention.

BACKGROUND OF THE INVENTION

Eye movement monitoring is gaining increasing importance in law enforcement and counter-terrorism, as well as psychiatric and other medical evaluative applications to evaluate the tendencies of, for example, sex offender, terrorists, psychiatric patients and others.

Current technology that attempts to identify the subject's interest may rely on measurements of where the subject is looking within an image (the overt attentional focus), or measurements of the duration that subjects look at a given image. Reaction time measures of viewing, questionnaires and direct interrogation, as well as direct eye position measurements (preferentially looking at items of interest) are examples of these measures. These technologies suffer from the problem that the subject is often aware that the measurements are being made and thus can easily misdirect the interrogator by intentionally or unintentionally looking at a given image for an inappropriate long or short duration, or by looking at irrelevant parts of the image.

Recently, eye movement monitoring is gaining increasing importance in the evaluation of interest that focus groups have in particular visual elements in commercial advertising. These analyses are also used in psychiatric and other medical applications to evaluate, for example, the tendencies of sex offenders and the progress of their therapeutic regimen. Thus, a reliable way to painlessly and non-invasively determine the position of secret military assets on a map, the actual position of covert interest of a consumer within a commercial advertisement, the position of a secret terrorist hiding place within a map, or the focus of deviant interest of a suspect within an image during a clinical or criminal investigation, will lead to huge advances in many fields.

SUMMARY

A method and apparatus are provided for identifying the covert foci of attention of a person when viewing an image or series of images. The method includes the steps of presenting the person with an image having a plurality of visual elements, measuring eye movements of the subject with respect to those images, and based upon the measured eye movements triangulating and determining the level of covert attentional interest that the person has in the various visual elements.

DETAILED DESCRIPTION OF AN ILLUSTRATED EMBODIMENT

Figure 1:
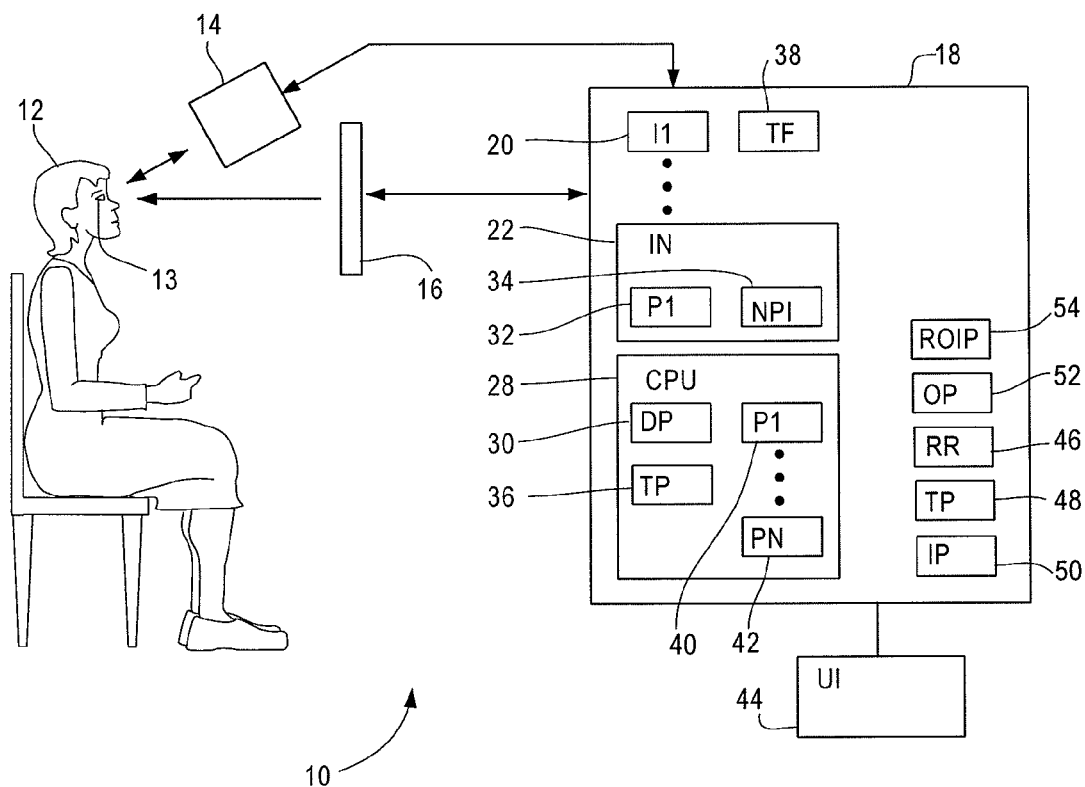
FIG. 1 depicts a system for identifying foci of attention shown generally in accordance with an illustrated embodiment of the invention.

Described herein is an innovative method to determine the position of covert attentional foci within images and sequences of images. The central idea is to extrapolate the trajectories of microscopic unconscious eye movements that occur during visual fixation, called microsaccades, to determine the position of covert attentional foci. Microsaccades are small involuntary saccades that occur when one attempts to fixate (hold the eye stationary) within an image. As rotations of the eye, microsaccades are more rapid than other types of fixational eye movements, and they travel in a relatively straight line across the image. Further, microsaccade rate and direction have been shown to be biased towards the position of covert attentional foci within an image. That is, no matter where one fixates on an image, the rate and direction of microsaccades is influenced by the presence and position of a target of interest on the image. A viewer may overtly attend the interesting target (by looking right at it) or covertly attend the target (by looking away from the target and secretly paying attention to the target). When covert attention is engaged, microsaccades are biased in a direction towards the attended region of interest in an involuntary and unconscious manner that we describe herein and which can be used as a method to objectively determine the position of covert attentional foci.

The underlying basis of the invention is that, by examining the trajectory of microsaccades and the durations of fixation and locations of the retinal fovea while subjects view images, blueprints or movies, the described system localizes areas of covert and overt interest in those images, even in the case that the subject is aware of what the test is for, and is unwilling to cooperate. Since microsaccades are involuntary and undetectable to subjects, these measurements of covert attention are accurate even if the subjects knows the purpose of the test, and even if they tried to overtly hide any points of interest. As such, the method herein is of immense utility in determining covert regions of interest painlessly, non-intrusively and transparently as compared to currently used tests. This innovation provides novel and highly accurate and cost-efficient assessments that address the level of threat of, among other things, sexual offenders, as well as areas in which treatment should be focused. Modified versions of these methods could be applied to various interrogatory fields of criminal justice, national defense, marketing and consumer interest in advertising or neurological and psychiatric medical evaluation.

The use of this method in evaluating sex offenders is presented as one example of the method's use, and not intended to limit the scope of the invention. Present-day tests of sexual arousal, such as the penile plethysmograph, and of sexual interest, such as viewing time tests, all suffer from problems with sensitivity, specificity, and transparency. Lie detectors suffer from the same problems. This has led to a gap in knowledge that has limited the efficacy of treatment programs and increased the risk of recidivism. Innovative and objective assessment instruments are therefore needed to improve the accuracy and reliability in the measurement of sexual interest. It has been determined that, by examining the trajectory of microsaccades and the durations of fixation of the macula (the retinal area of sharpest focus) while offenders and non-offenders view photographs of variously aged individuals of potential sexual interest, it is possible to localize areas of covert sexual interest.

The methods and system described examine the role of eye movement trajectories in detecting objective covert in combination with overt areas of interest. One outcome of this method is that eye movement dynamics are shown to discriminate between sex offenders and non-offenders during both the fixational and free-viewing paradigms, distinguish types of offenders, and do so more accurately and with higher cost-efficiency than tests now in use. The significance of this specific use of the method is that it produces a safe, non-intrusive and non-transparent method for determining the covert and overt points of sexual interest within a scene.

In an exemplary embodiment, one objective of invention is to determine the overt and covert loci of attention through free viewing analysis of images. In this context, overt loci are a series of points within the center of an individual's gaze. In contrast, covert loci are those not in the center of an individual's gaze.

Another feature is the ability to determine the covert loci of attention through fixational analysis of images. This feature tests the hypotheses that specific covert regions of interest within images will attract greater microsaccade directional bias than areas of non-interest. Moreover, the method can be used to distinguish groups of subjects. For example, sex offenders will exhibit more covert interest in specific parts of specific sexually charged scenes than will non-offenders. As such, a subject can be characterized as needing further treatment, or not, through the analysis of eye movements described herein, such as by allowing subjects to freely view charged scenes.

A second application may include guided viewing of dual images where subjects fixate on a randomly moving point while viewing a pair of images, as above. This way of viewing determines, for instance in sexual offenders, whether offenders demonstrate microsaccade bias in the direction of one scene over the other and in specific regions of interest when compared to non-offenders through triangulation. The hypothesis is that the pattern of microsaccadic directional bias and rates allow the location of specific areas of interest that differ between the offender and non-offender groups and allow a user to distinguish type of offender as well.

A third application can include the central fixation of dual images where subjects fixate on a central point between image pairs, as above. Eye positions may be tracked to determine directional bias. This procedure identifies covert points of interest even when the subject rejects the free-viewing paradigm of described above. The hypothesis is that offenders or other subjects under observation or interrogation will covertly modulate eye direction toward the deviant image within the pair when compared to the non-offenders or control subjects and that directional bias also distinguish offenders or other subjects under observation or interrogation as to type.

Turning, in general, now to illustrated embodiments of the invention, FIG. 1 shows a system 10 for detecting eye movement as an objective measurement of covert attentional loci under an illustrated embodiment of the invention. Included within the system 10 may be an eye tracking device 14, such as the EyeLink II by SR Research (http://www.sr-research.com/fixed_tech_spec.php) or other equivalent eye tracking systems such as the IVIEW™ HI-SPEED 1250 tracking system by SensoMotoroic Instruments (http:www.smivision-.com/en/eye-gaze-tracking-systems/products/iview-x-hi-speed.html). Also included within the system 10 may be a display 16 and host 18.

While the methods used and system 10 will be described in the context of sexual offenders, the system 10 could just as easily be used in other contexts. For example, other tests could be developed for any group of person having covert attentional interest in an image. This would apply to other types of criminals, political enemies, consumers interested in specific aspects of commercial products, neurological or psychiatric patients. The only requirement is the identification and use of the appropriate visual stimulus.

A display processor 30 within a controller 28 of the system 10 may retrieve one or more image files 20, 22 from a memory and present the images to a person 12 on the display 16 either statically or dynamically. Each of the image files 20, 22 may include one or more elements 32, 34 along with the coordinate positions of the elements 32, 34 within each of the images 20, 22. Where the images 20, 22 are presented dynamically, the display processor 30 may maintain an image table of image data including current positional information (e.g., x-y coordinates) for each of the elements 32, 34 as they are moved around the display 16.

As the images 20, 22 are presented to the person 12, the eye tracking device 14 detects the position and movement of the eyes 13 of the person 12. A tracking processor 36 within the host 18 may receive the position of the eyes 13, a distance between the person 12 and display 16 and calculate a center of the field of view of the eyes 13 on the display 16 under an appropriate coordinate system (e.g., x-y coordinates of the eye position on the display 16). Once calculated, the tracking processor 36 retrieves the then-current image table from the display processor 30 and combines the data as a snapshot in time of eye position versus image data and saves the data in a file 38.

Figure 2:
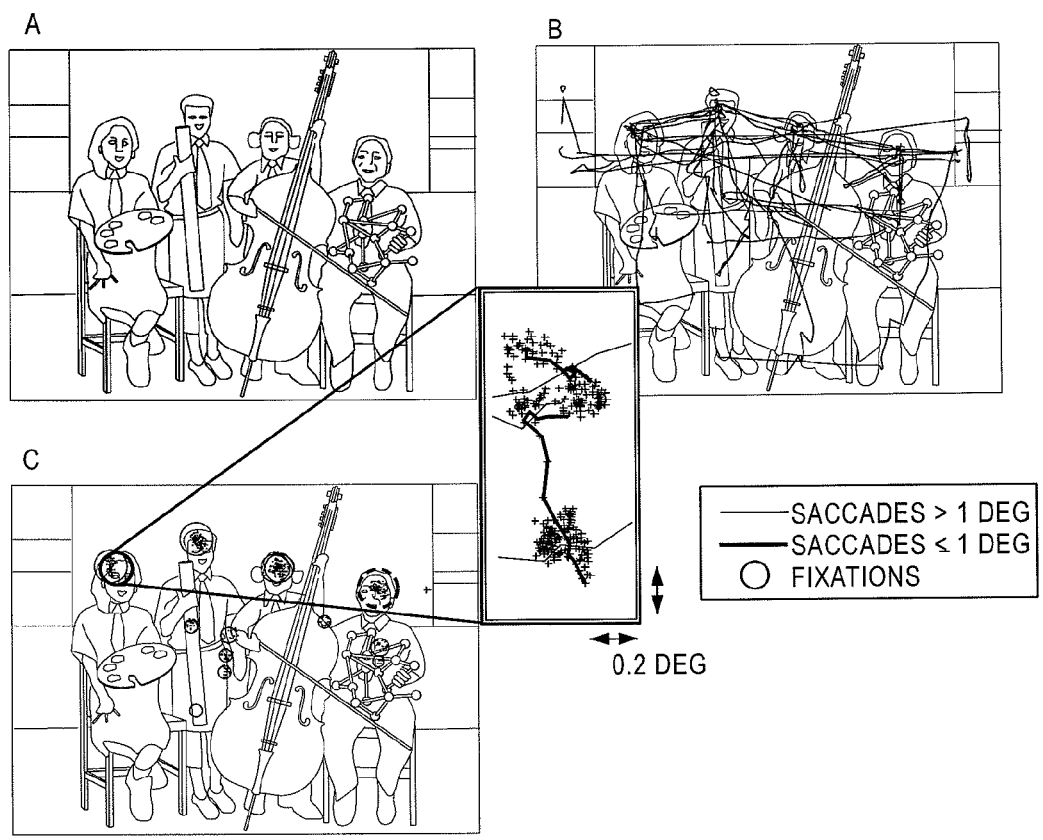
FIG. 2 depicts images with eye movements tracked by the system of FIG. 1.

Also included within the controller 28 may be one or more programming modules 40, 42 that process the positional information about the eyes 13 to detect microsaccades and macular fixation. For example, FIGS. 2A-C show a time-elapsed image with eye position in the context of free viewing that may be displayed on a terminal 44 of a user of the system 10. FIG. 2A presents the image equalized for luminance and contrast. FIG. 2B shows a 45 second eye position trace during free visual exploration by a person, plotted over a low-contrast version of the image of FIG. 2A (for clarity). FIG. 2C is a 10 second period from FIG. 2B. The area of each circle in FIG. 2C indicates the duration of the fixation period (smaller circles correspond to fixations of shorter duration). The largest circle corresponds to a 1,678 ms fixation period. As shown, human faces attracted long-duration fixations in this normal subject and proved to be a primary focus of microsaccades in this image.

Turning now to the system 10 in particular, a more specific explanation will be provided of the use of the system. A first example involves the overt and covert loci of sexual interest of offenders through free viewing of images. More specifically, the first example provides a test that determines whether subjects, such as sex offenders, who volunteer as willing subjects freely view and overtly examine points of interest within sexually charged images for longer durations than non-offenders. Subjects will freely view images (described below) as their eyes are tracked to determine fixation positions and durations within each scene, both of which are under voluntary control, indicating overt attentional loci. Microsaccade rate and direction are measured during fixation periods. These dynamics of microsaccades are under involuntary control and indicate covert attentional loci. In addition, regions of all images will be divided into a number of different elements (e.g., face, chest, genital area, legs, etc.). The underlying hypothesis incorporated by the system 10 is that offenders will demonstrate longer durations of fixation on deviant sexual points of interest within images, such as the genital area of children, than will non-offenders. A first part of the test determines whether the offenders do or do not demonstrate longer overt fixations than normal people. As a second part of the test, the system 10 will also determine the directional bias of microsaccades during fixation periods to triangulate covert areas of sexual interest. In order to increase the accuracy of eye measurements, subjects 12 are stabilized with a chin rest to maximize stability. They then alternately view images consisting of photographs of models of both genders in sexually aggressive scenes of various levels of severity. In all scenes, for the purpose of this specific use, the models of the images 20, 22 will be in swimsuits, underwear or revealing clothing. The viewing time for each image by the person 12 may be 45 seconds and each screen may be standardized as to luminance, background and proportional size in this and succeeding examples.

Another example may include free-viewing of dual images where the person 12 may freely view paired images (e.g., one image of low interest and the other with higher interest). Viewing image pairs facilitates direct comparisons between eye movement positions and dynamics in the two different levels of interest. This example, if applied to sexual offenders, determines which areas and body regions within the image offenders prefer to overtly view, as well as the class of image that they prefer, as compared to a reference non-offending group. The system 10 simultaneously tracks eye position to determine fixation positions and durations within each scene, both of which are under voluntary control and hence indicate overt attentional loci. In addition, microsaccade rate and direction will be measured during fixation periods. These dynamics are under involuntary control and thus indicate covert attentional loci. The rational used by the system 10 is that offenders will overtly fixate on sexually-related regions of deviant images for longer periods than non-offenders, and that the directional bias of microsaccades during fixation periods offer the opportunity to triangulate covert areas of sexual interest.

In another example, the person views image pairs 20, 22 as described below. The pairs of images 20, 22, in the case of its application to sex offenders, consist of a deviant stimulus, such as sexually charged image of a child, preteen, teen, or aggressive sexual activity on one side of the screen 16 and a sexually charged (non-deviant) image of an adult on the other side. Sides will be randomly alternated to correct for any right-left bias in this and succeeding examples. The objective of this example is to determine the covert loci of sexual interest through fixational analysis of images. This example tests whether the person 12 will produce microsaccade dynamics that reveal covert points of sexual interest within sexually charged images to a greater extent than non-offenders. To address this, persons 12 are subjected to three tests: 1) a guided viewing of single images where the person views a fixation point (a small cross) that moves randomly across the screen. The system 10 tracks eye positions to determine whether the microsaccade rate and direction measurements taken from the previous example are replicable during these passive viewing conditions. The rationale is that offenders will covertly modulate their microsaccade rate and direction toward deviant stimuli, and regions within them, to a greater extent than non-offenders, and that different types of offenders can be distinguished as to type of offender through these measurements. As in the previous test, subjects 12 alternately view the sexually charged images of all levels of severity in addition to sexually aggressive scenes. The presentations of these single stimuli is randomized with regard to age, gender and order of presentation.

Another test may include the use of guided viewing of dual images in which each subject views a fixation point that moves randomly over the same paired images shown to each subject in the test. The system 10 will track eye positions simultaneously to determine whether the microsaccade rate and direction measurements from the previous experiment are replicable during these passive viewing conditions. The rationale is that offenders covertly modulate their microsaccade rate and direction to indicate deviant regions of interest to a greater extent than non-offenders and that offenders can be distinguished as to type through these measurements.

In this test as with the previous test, subjects will view the pairs of sexually charged images, each pair consisting of a deviant stimulus on one side and a non-deviant stimulus on the other. The pairs will usually consist of a sexually charged image of a child on one side and an adult on the other side; or an aggressive sexual scene on one side as compared to a less charged scene on the other side.

Another example includes central fixation of dual images where subjects view a fixation point that is stationary and centered on the screen as described in the previous tests. Each subject will be instructed to fixate and the system 10 will track eye positions to determine whether the microsaccade directions are biased towards images of deviant sexual interest. The reason is that offenders covertly modulate their microsaccade direction to indicate interest in deviant images and in sexually interesting regions within deviant stimuli to a greater extent than non-offenders. Another reason is that offenders can be distinguished as to type through these measurements. As in previous tests, subjects view the image pairs described above.

In general, subjects 12 will examine an image in which the user (the interrogator, therapist, experimenter, investigator, etc) wishes to locate regions of interest (ROIs) of the person 12. These ROIs are foci of covert attentional interest that each subject indicates with the direction of his/her microsaccades. These microsaccades are determined from each subject's eye position traces over time in files 38, and trajectories extrapolated from these microsaccades are triangulated to indicate loci of attention.

Each subject's eye movements are detected by the eye tracking system 14. Any eye tracking system available in addition to those discussed above can be used for this purpose (e.g., video tracking, scleral search coil, etc.). The temporal and spatial resolution of the eye tracking systems should be high enough to allow microsaccade detection. A sampling rate higher than 500 Hz is generally used although microsaccades can nevertheless be detected with lower rates at the expense of suboptimal performance.

The objective of the data collection is to acquire enough microsaccades to triangulate the location of the ROI using several possible algorithms. The fundamental information needed is the position and the direction of the microsaccades. Best accuracy of the triangulation can be obtained if multiple microsaccades are produced in at least three different locations around the ROI. Therefore, the subject will optimally fixate evenly across the entire image to collect microsaccades that enable the identification of any possible ROI. To achieve this outcome several options are available depending on the cooperation level of the subject.

A first option is to use guided fixation across the image. A fixation spot indicates where the subject should fixate. The location of the fixation spot changes either randomly or systematically to obtain an optimal distribution of microsaccades across the image.

Another option is to use static fixation with movement of the image. The subject fixates continuously at the same spot and the image and the background moves, again, randomly or systematically producing enough fixation time in each area of the image.

A third option is to use free viewing. The subject is simply asked to look around the entire image.

Still another option is to use free viewing with random movement of the image. In the case the previous method does not achieve a proper distribution of microsaccades for whatever reason, such as when the subject is non-cooperative, an even distribution of eye positions across the image can be achieved by moving the image around the display irrespective of eye position until the entire image has been evenly tiled.

The algorithm for detection of the ROI can be applied in real time, while the data is being collected, or offline when all the data has already been collected. In the first case the algorithm can also indicate when enough data has been collected to stop the data collection. In both cases, online and offline, the algorithms will otherwise function in the same way.

The first step in the process is to detect the microsaccades in the eye movement trace. As noted above, any method to detect eye position (video, eye coil, optical, etc) and microsaccades can be used. Two main algorithms have been used in the literature to detect microsaccades objectively from eye position traces: Martinez-Conde and Macknik algorithm (Martinez-Conde and Macknik algorithm (Martinez-Conde S., Macknik S. L., Hubel D. H. (2000) Nature Neuroscience) and Engbert algorithm (Engbert algorithm (Engbert R., Kliegl R. (2003) Vision Res 43:1035-1045.), all of which are incorporated herein by reference. The principal advantage of Engbert algorithm is that it adapts to the level of noise of the data. However while this improves its performance in noisy situation, the Engbert algorithm can produce non optimal results in low noise conditions where the Martinez-Conde and Macknik algorithm behaves better.

Next, the position of the microsaccade in the image and its direction is calculated by a microsaccade processor. The position is the starting point of the microsaccade and the direction is the angle of the line that crosses the starting and ending point of the microsaccade.

Finally, it is possible to use several algorithms (embodied as one or more program modules 40, 42) to determine the ROIs using the information provided by microsaccade location and directions.

Figure 3:
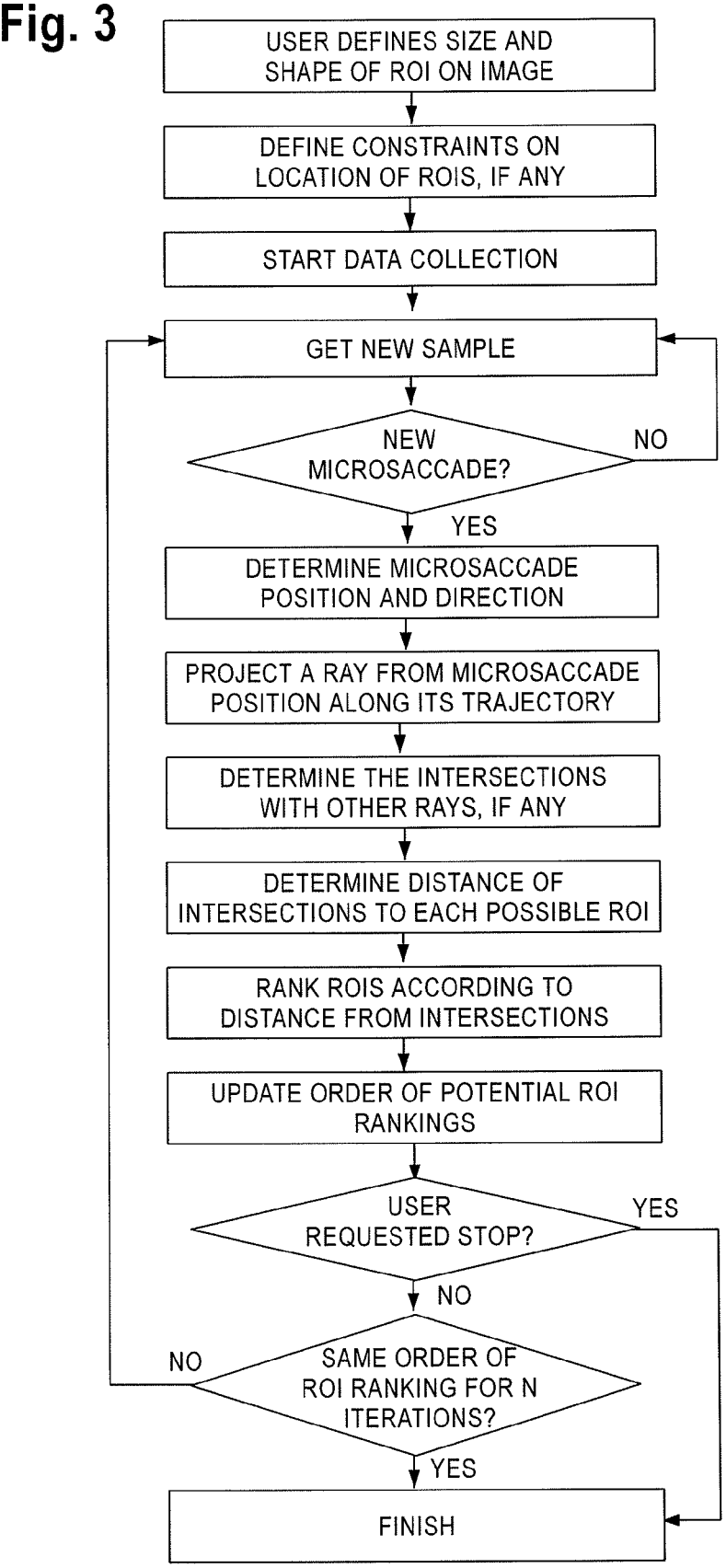
FIG. 3 depicts a first process for identifying regions of interest that may be used by the system of FIG. 1.

FIG. 3 depicts the operative features of a first program module 40, 42. While FIG. 3 is depicted in the form of a flow chart, the elements of FIG. 3 also represent the individual subroutines (and the medium on which the subroutines operate) used to accomplish the purpose of the process of FIG. 3.

Figure 6:
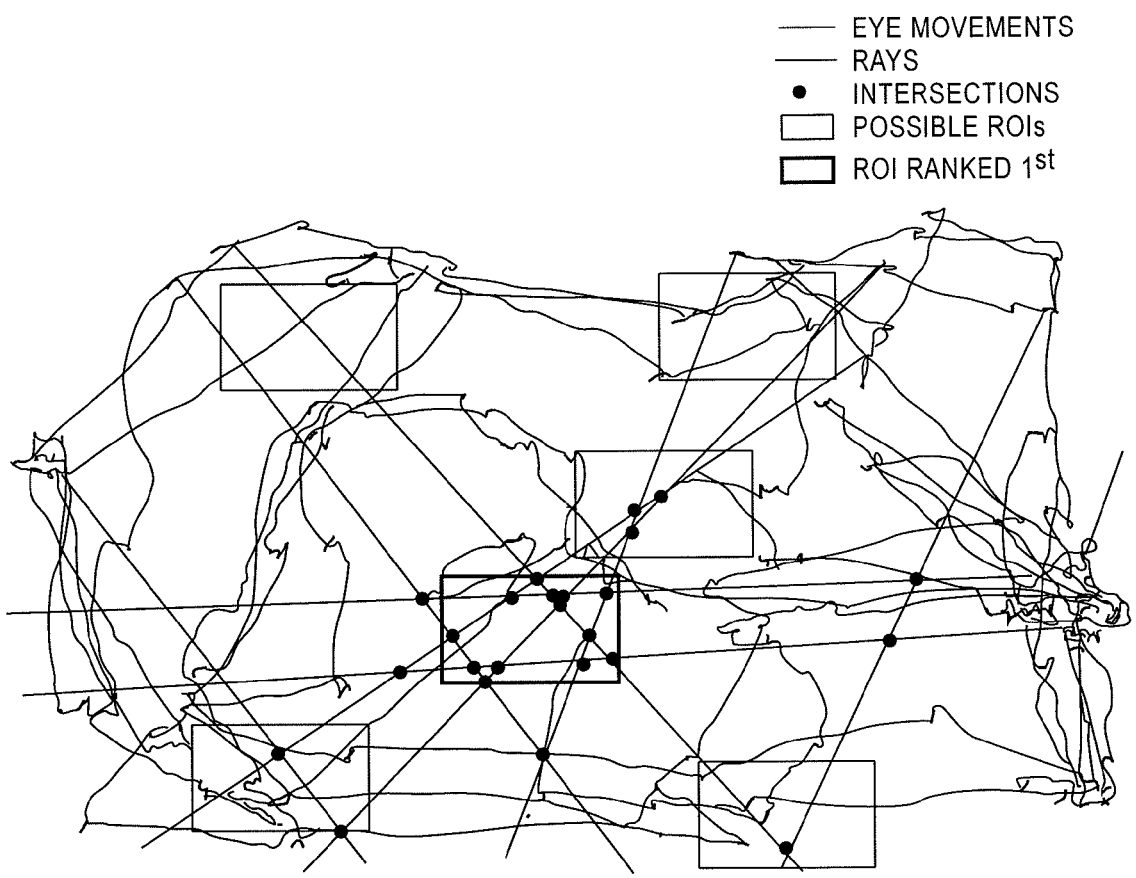
FIG. 6 depicts regions of interest that may be identified by the process of FIG. 3.

In FIG. 3, a supervising user defines ROI parameters through the terminal 44 on an image 20, 22 as shown in FIG. 6. In this case the user can decide the size of the ROI and the constraints of where the element can be found on the image (s). The program module 40, 42 will test every pixel of the image if no constraints are provided. For each microsaccade, a ray processor 46 calculates a ray that is parallel and coincident with the microsaccade. The ray is projected starting at the position of the microsaccade following its direction within the limits of the image. Then, all the locations in which the rays intersect are determined by an intersection processor 50. All possible regions of interest are tested and ranked by the distance from the intersections by an ordering processor 52. The program module 40, 42 can stop when it reaches a stable rank for the possible regions or when the user determines that enough data has been collected. The distance score may vary based on the type of distance calculation employed (i.e. Euclidean distance, hamming distance, non-linear distance calculations, etc.). The determination of a likelihood of interest may be based upon some threshold value of intersecting rays.

Figure 4:
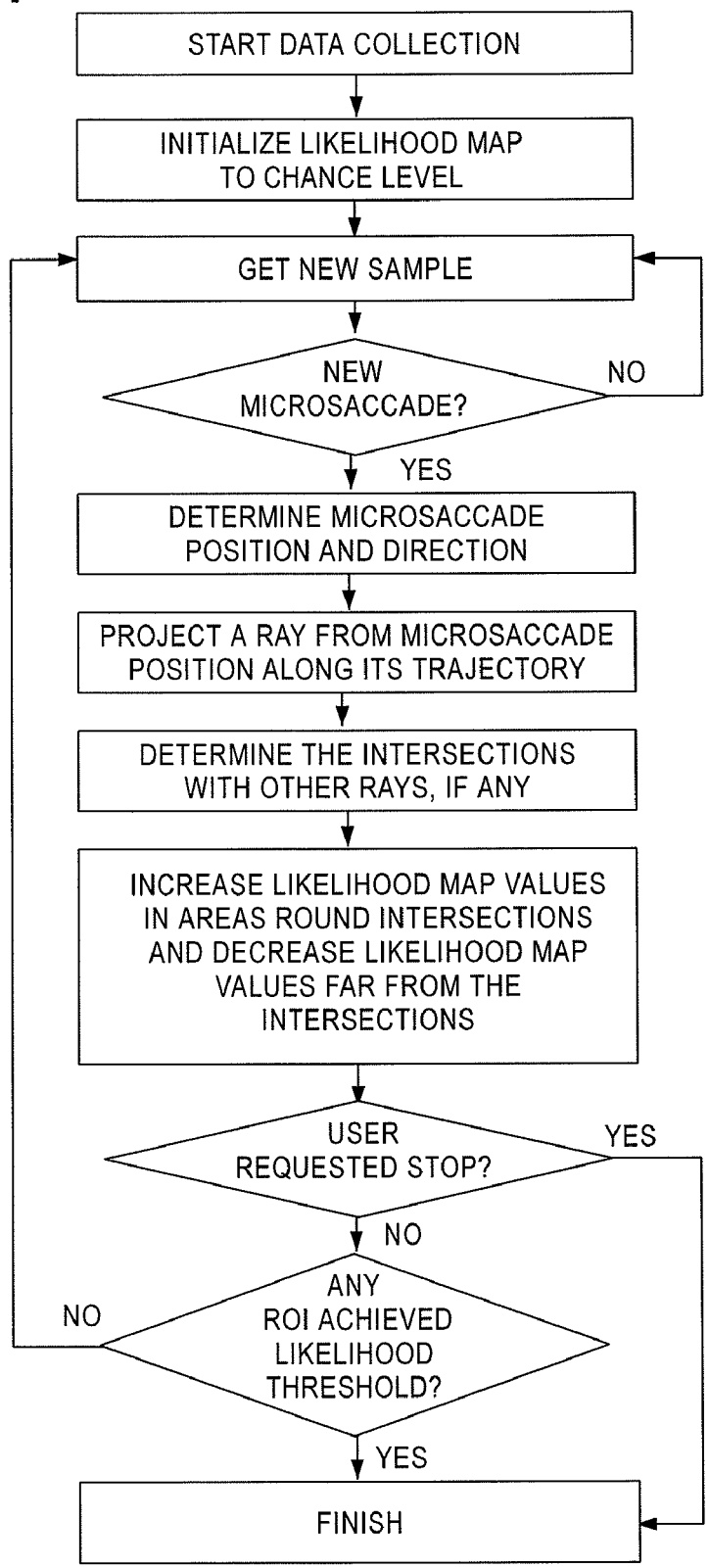
FIG. 4 depicts a second process for identifying regions of interest that may be used by the system of FIG. 1.

FIG. 4 depicts the operative features of a second program module 40, 42. While FIG. 4 is depicted in the form of a flow chart, the elements of FIG. 4 also represent the individual subroutines (and medium on which the subroutines operate) used to accomplish the purpose of the process of FIG. 4.

Figure 7:
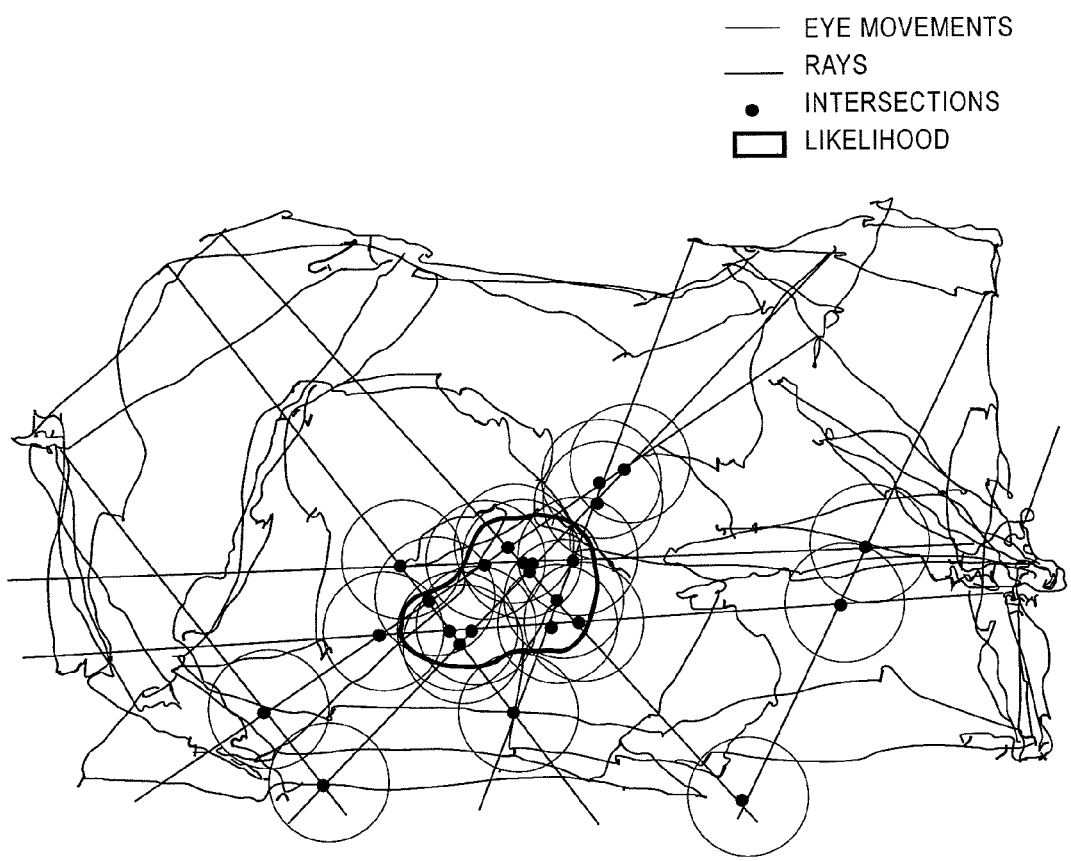
FIG. 7 depicts regions of interest that may be identified by the process of FIG. 4.

In the second program module 40, 42, the ROI parameters are unknown a priori (i.e., the second program module is based on intersection of trajectories). Rays and intersections are determined using the same method as in the first program module. However, in this case there is no prior information about the size or location of the ROI. Every pixel of the image has a value that indicates the likelihood or being part of the ROI. The user initializes this value at a chance level (0.5). Then, for each new intersection a ROI processor 54 of the system 10 increases the likelihood of the pixels nearby and decrease the likelihood of the pixels far away and displays this information on the terminal 44 as shown in FIG. 7. The locations where these intersections concentrate will have a higher likelihood of interest for the subject 12. The relationship between distance to the intersection and increase or decrease in likelihood of interest can be any function with a maximum at the intersection and a monotonically decreasing value around it. Different possibilities for a stopping condition are: 1) stop when just one pixel reaches the predetermined likelihood threshold; 2) stop when a certain number of contiguous pixels reach the predetermined likelihood threshold or 3) the user determines that enough data is collected.

Figure 5A:
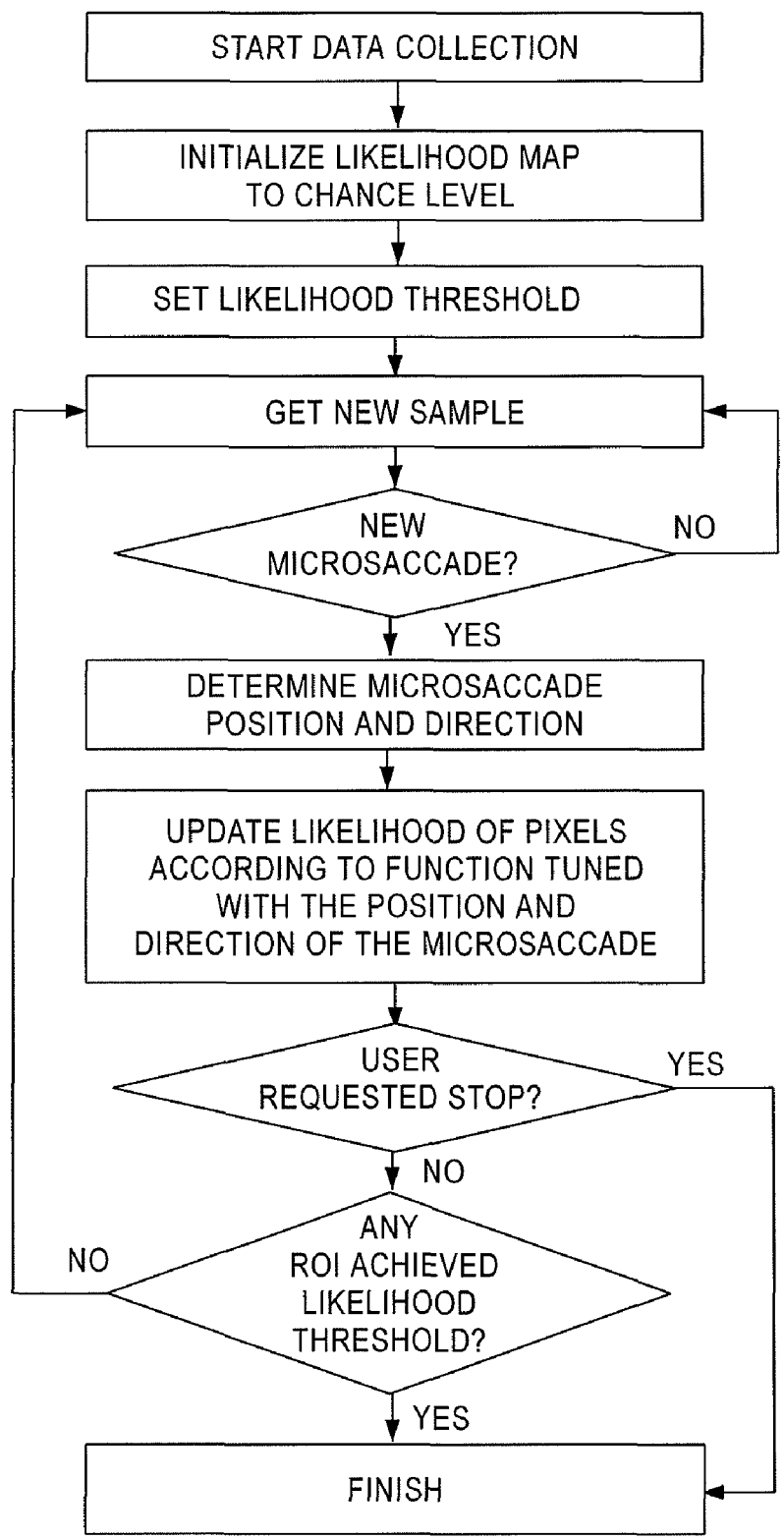
FIG. 5A-B depicts a third process for identifying regions of interest that may be used by the system of FIG. 1.
Figure 5B:
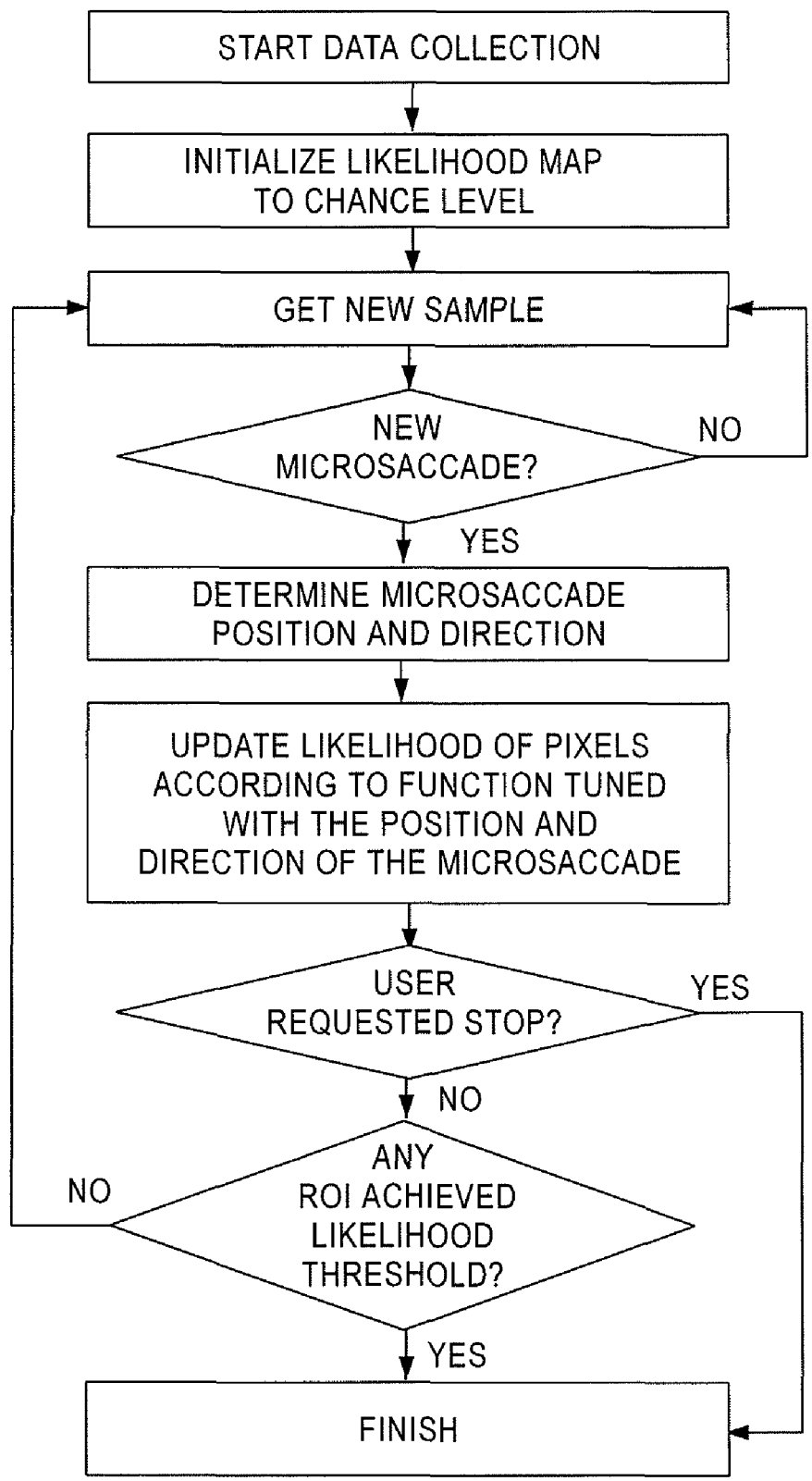

FIG. 5 depicts the operative features of a third program module 40, 42. While FIG. 5 is depicted in the form of a flow chart, the elements of FIG. 5 also represent the individual subroutines (and medium on which the subroutines operate) used to accomplish the objective of the process of FIG. 5.

Figure 8:
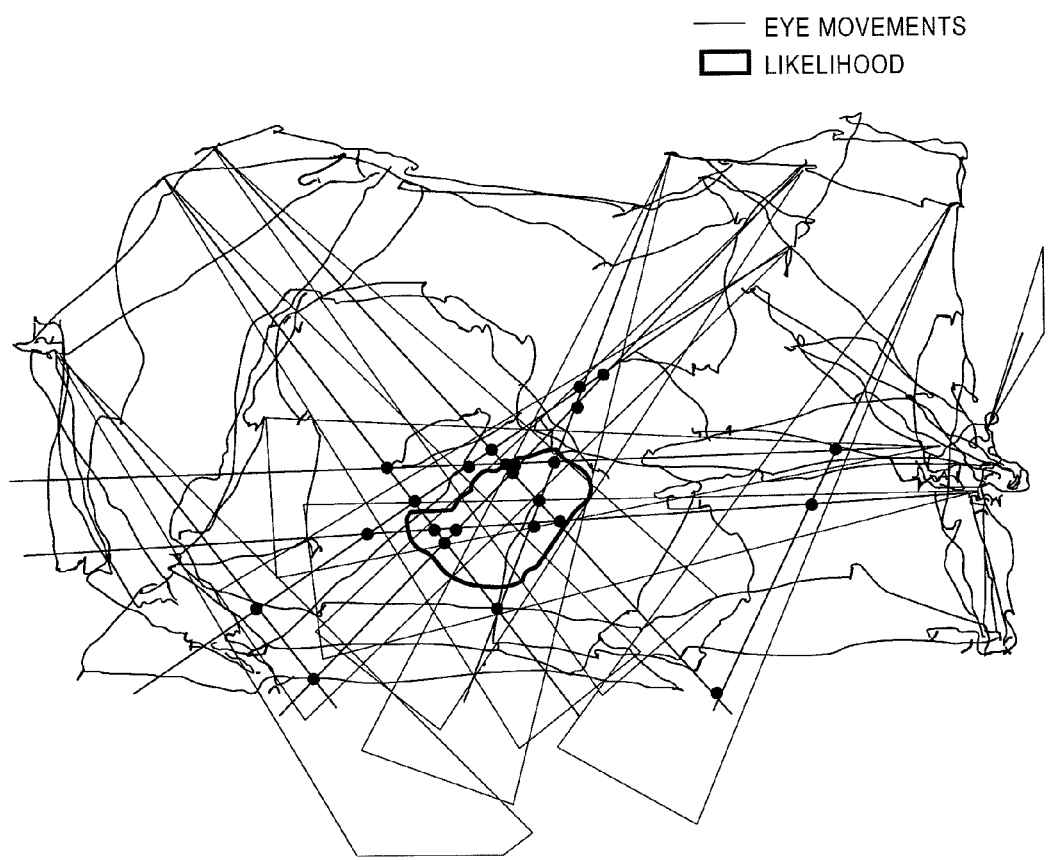
FIG. 8 depicts regions of interest that may be identified by the process of FIGS. 5A-B.

In FIG. 5, the ROI parameters are unknown a priori to the third program module. In this case, the third program module determines the ROI based on triangulation taking microsaccade trajectory error into account, as shown in FIG. 8. In this case, the ray diverges from the source microsaccade to incorporate any detection error in eye position.

Every pixel of the image has a value that indicates the likelihood of being part of the ROI. The system 10 initializes this value at a chance level (0.5). Then, for each new microsaccade the system 10 increases or decreases the likelihood (scalar value) of each pixels of the image according to a function that varies with the location and direction of the microsaccades (and intersection of diverging rays). This function increases the likelihood of incorporation of the pixels that are close to the ray projected from the position of the microsaccade along its direction. Different possibilities for a stopping condition are: 1) stop when just one pixel reaches the predetermined likelihood threshold; 2) stop when a certain number of contiguous pixels reach the predetermined likelihood threshold or 3) the user determines that enough data is collected.

The program modules 40, 42 may also embody one or more microsaccade detection algorithms (e.g., Engbert algorithm (Engbert R., Kliegl R. (2003) Vision Res 43:1035-1045). First, the time series of eye positions is transformed to velocities by a sample tracking processor 48 that calculates a velocity vector $\vec{v}_n$, according to the expression, $$\vec{v}_n = \frac{\vec{x}_{n+2} + \vec{x}_{n+1} - \vec{x}_{n-1} - \vec{x}_{n-2}}{6\Delta t},$$

which represents a moving average of velocities over 5 data samples to suppress noise. As a consequence of the random orientations of the velocity vectors during fixation, the resulting mean value is effectively zero. A multiple of the standard deviation of the velocity distribution is used as the detection threshold. Detection thresholds are computed independently for horizontal and vertical components and separately for each trial, relative to the noise level.

The ray processor 46 calculates a ray from the velocity vector. In this case, the ray processor determines the ray by forming a line parallel to the velocity vector across the respective images. The ray module may also calculate a diverging ray (shown in FIG. 8) to accommodate the errors in eye detection accuracy. In this case, the expanded ray extends from a root of the velocity vector and extends along the velocity vector where the expanded ray diverges on each side of the velocity vector by the detection error.

Typical values for the detection threshold of microsaccades are 4, 5 or 6 times the standard deviation of the velocity. Therefore, the algorithm is robust with respect to different noise levels between different trials and subjects. Additionally, minimum microsaccade duration of 8 or 12 ms is required to further reduce noise.

Finally, either binocular microsaccades, microsaccades with at least 1 sample of overlap between the two eyes (e.g., Martinez-Conde and Macknik algorithm (Martinez-Conde S., Macknik S. L., Hubel D. H. (2000) Nature Neuroscience), or monocular microsaccades may be employed. However, binocular microsaccades are expected to produce more accurate data (Martinez-Conde S., Macknik, S. L., Troncoso X. G., Dyar T. A. (2006) Neuron). The first step is the differentiation of the data (horizontal and vertical position), so that each element represents the instantaneous velocity of the eye in horizontal and vertical space, then data is smoothed with a 31 ms-wide unweighted boxcar filter to reduce noise.

Then, the direction and size of the motion between each two samples is calculated. The size of the motion represents the velocity of movement in polar coordinates and the direction is differentiated to obtain the rate-of-turn indicator.

The algorithm will determine if the eye is moving when the polar velocity is more than 3° per s and the rate-of-turn is smaller than 15°. Finally only detected eye movements of more than 3 arcmin and less than 2° are considered microsaccades.

The above system 10 and method has significant implications for criminal justice policy and practice. At present, policy decisions made at federal, state, and local levels have been based upon the results of available social science and psychological research along with the amount of media attention that spectacular but atypical cases attain. These results should not to be confused with objective means of determining sexual offending risk and response to treatment. Clinicians are often called upon to render opinions in these crucial areas based upon soft scientific data. These opinions and decisions, reached not only by clinicians, but secondarily by prosecutors, judges, juries, and parole and probation officers, can impact an individual's freedom and constitutional rights and, more importantly, the safety of entire communities.

The four tests upon which such offender decisions now rest are the polygraph, the penile plethysmograph, and two preexisting viewing time tests, the Abel Assessment for Interest in Paraphilias and the Affinity Test. The difficulties inherent in these assessment instruments have been well documented in many review articles. First, the polygraph has not proven useful in determining sexual interest or in predicting recidivism among sexual offenders. Second, the plethysmograph is highly intrusive, expensive and time-consuming and is inherently insensitive. It is not often used for those under 18 years of age and is restricted to males. It cannot distinguish offenders who have molested young children or adolescents or have committed rapes from non-offenders. Third, the preexisting viewing time tests have not been validated with a non-offending population, have been tested mostly within the originators' laboratories, are inherently transparent and thus of decreasing utility, and have never been shown to predict recidivism. They require extensive computer expertise and a lengthy learning time. They also have failed to differentiate differing types of offenders in the crucial areas of sexual crimes against young girls and adult women.

The above system 10 provides a method and apparatus that discriminates not only between offenders and non-offenders, but also discriminates among offenders (e.g. rapists from heterosexual pedophiles from homosexual pedophiles, etc.) and which are nontransparent and thus difficult or impossible to manipulate. The system 10 provides a novel means of assessing sexual interest. It is based upon observations that individuals tend to shift their eyes to an object of sexual interest even while instructed to gaze elsewhere. Moreover, individuals are unaware of such tiny eye movements, each measured in the millisecond range.

The system 10 provides a mechanism by which eye movement tests are capable of discriminating sexual offenders from non-offenders, and discriminating the types of sexual stimuli of interest to each offender. The system 10 provides the field of sexual offender assessment and treatment with an objective, non-transparent tool which is of much greater predictive and clinical utility than currently available methods or instruments. This finally enables clinicians and judicial officials to render judgments and decisions affecting individuals and communities with far greater accuracy.

As suggested above, the system 10 could be used in any of a number of other circumstances. For example, in the case of a terrorist, the system 10 could be used to display a map to the terrorist to determine the location of terrorist or enemy combatant weapons. Once presented with the map, the system 10 could be used to record eye position and areas of high attentional interest on the map (such as potential caches of weapons) to identify possible sources of risk.

The system could also be used to benefit a psychiatric patient. In this case, the system 10 could be used to determine or quantify the level of attention that psychiatric patients have in specific image elements of a psychiatric chart, so as to maximize the effect of therapy. For example, a patient may have an abnormal phobia of snakes. In this case, the image may include a number of psychiatric trigger elements (e.g., snakes, spiders, etc.). The level of abnormal attention that the patient has towards snakes, as opposed to other types of creatures, could be assessed with the system 10 herein. Then, therapy could be given to the patient to ameliorate their fear of snakes, and the level of effectiveness of the therapy could be assessed by retesting the same patient's level of attention to snakes after therapy. End points in therapy, or necessary newly prescribed therapies, could then be enacted on this basis.

On still another level, the system 10 could be used with ordinary consumers. In this case, the system 10 could be used to determine the location of high consumer interest in an advertisement, product, or televised or cinematic program.

For example, a movie production company may optimize the efficacy of a film's advertisement by using the system described herein to determine rank order of interest that consumers have in the specific celebrities starring in a movie. An image containing photographs of all of the celebrities in the movie could be presented to a focused consumer group of known demographics and overt and covert attentional eye movement analysis would reveal which of the celebrities the consumers attended to in order of level of interest. The celebrities chosen to represent the movie on the poster could then be chosen from the top of the list so as to optimize the advertisement's efficacy.

A specific embodiment of method and apparatus for identifying the covert foci of a person has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

The invention claimed is:

1. A method of identifying the covert foci of attention of a person comprising:
   presenting the person with an image having a plurality of visual elements;
   detecting trajectories of microsaccadic eye movements of the subject with respect to the image; and
   associating the eye movements with a visual element of interest within the plurality of elements by extrapolating the trajectories of at least some of the detected eye movements to an area of intersection in the image to determine an area of covert attentional focus.

2. The method of identifying the covert foci of attention of the person as in claim 1 further comprising measuring a duration of microsaccadic eye movements of the subject and combining information from the duration measurement with information from the trajectories of the detected eye movements to determine an area of covert attentional focus.

3. The method of identifying the covert foci of attention of the person as in claim 1 wherein the step of associating the eye movements with the element further comprises triangulating trajectories of the microsaccades to a location of the associated visual element on the image.

4. The method of identifying the covert foci of attention of the person as in claim 1 wherein the step of associating eye movements with the element further comprises associating the eye movements with a plurality of elements of the image and ordering the elements of the image based upon the number of intersecting trajectories of the microsaccades associated with each of the respective visual elements.

5. The method of identifying the covert foci of attention of the person as in claim 1 wherein the step of associating the eye movements with the element further comprises triangulating trajectories of the microsaccades to locations on the image and increasing a weighting of pixels proximate each intersection and decreasing a weighting of pixels relatively far from the intersections.

6. The method of identifying the covert foci of attention of the person as in claim 1 wherein the step of associating the eye movements with the element further comprises triangulating a set of diverging trajectories of the microsaccades to locations on the image and increasing a weighting of pixels proximate each intersection and decreasing a weighting of pixels relatively far from the intersections.

7. The method of identifying the covert foci of attention of the person as in claim 1 further comprising classifying elements of the image within one of the group consisting of various levels of interest.

8. The method of identifying the covert foci of attention of the person as in claim 7 wherein the image further comprises elements classified as one of a group consisting of sexually deviant images.

9. The method of identifying the covert foci of attention of the person as in claim 8 wherein the image further comprises elements selected from a group consisting of various levels of deviant sexual interest in children.

10. The method of identifying the covert foci of attention of the person as in claim 8 wherein the image further comprises various levels of deviant sexual interest in adults.

11. The method of identifying the covert foci of attention of the person as in claim 7 wherein the image further comprises a map, blueprints or images with a plurality of map, blueprints or image presenting various levels of interest for a terror suspect, criminal or a person identified as a security risk.

12. The method of identifying the covert foci of attention of the person as in claim 7 wherein the image further comprises a psychiatric chart with a plurality of psychiatric or neurological trigger elements presenting various levels of interest for a psychiatric or a neurological patient.

13. The method of identifying the covert foci of attention of the person as in claim 7 wherein the image further comprises a marketing or consumer interest display with a plurality of marketing or consumer interest items presenting various levels of interest for a consumer.

14. The method of identifying the covert foci of attention of the person as in claim 1 further comprising presenting a plurality of images side-by-side.

15. The method of identifying the covert foci of attention of the person as in claim 2 further comprising guiding an eye fixation spot across the image where the fixation spot indicates where the person should fixate their gaze where the fixation spot changes either randomly or systematically to obtain a relatively optimal distribution of microsaccades across the image.

16. The method of identifying the covert foci of attention of the person as in claim 15 further comprising providing a static fixation spot where the static fixation spot indicates where the person should fixate their gaze and where the fixation spot moves randomly or systematically producing a predetermined amount of fixation time on each of the plurality of images.

17. An apparatus for identifying a covert foci of attention of a person comprising:
   means presenting the person with an image having a plurality of visual elements;
   means for detecting trajectories of eye microsaccades of the subject with respect to the image; and
   means for associating the eye movements with a visual element of interest within the plurality of elements of the image by extrapolating the trajectories of at least some of the detected eye movements to an area of intersection in the image to determine an area of covert attentional focus.

18. The apparatus for identifying the covert foci of attention of the person as in claim 17 wherein the means for associating the eye movements with the element further comprises means for triangulating trajectories of the microsaccades to a location of the associated visual element on the image.

19. The apparatus for identifying the covert foci of attention of the person as in claim 17 wherein the means for associating eye movements with the element further comprises means for associating the eye movements with a plurality of elements of the image and ordering the elements of the images based upon the number of intersecting trajectories of the microsaccades associated with each of the respective visual elements.

20. The apparatus for identifying the covert foci of attention of the person as in claim 17 wherein the means for associating the eye movements with the element further comprises means for triangulating trajectories of the microsaccades to locations on the image and increasing a weighting of pixels proximate each intersection and decreasing a weighting of pixels relatively far from the intersections.

21. The apparatus for identifying the covert foci of attention of the person as in claim 17 wherein the means for associating the eye movements with the element further comprises means for triangulating a set of diverging trajectories of the microsaccades to locations on the image and increasing a weighting of pixels proximate each intersection and decreasing a weighting of pixels relatively far from the intersections.

22. The apparatus for identifying the covert foci of attention of the person as in claim 17 further comprising means for classifying elements of the image within one of the group consisting of various levels of interest.

23. The apparatus for identifying the covert foci of attention of the person as in claim 22 wherein the image further comprises elements classified as one of a group consisting of sexually deviant images.

24. The apparatus for identifying the covert foci of attention of the person as in claim 23 wherein the image further comprises elements selected from a group consisting of various levels of deviant sexual interest in children.

25. The apparatus for identifying the covert foci of attention of the person as in claim 23 wherein the image further comprises various levels of deviant sexual interest in adults.

26. The apparatus for identifying the covert foci of attention of the person as in claim 17 wherein the presented images further comprise elements classified as one of the group consisting of sexually deviant images.

27. The apparatus for identifying the covert foci of attention of the person as in claim 17 wherein the image further comprises a map, blueprints or images with a plurality of map sites, blueprints or images presenting various levels of interest for a terror suspect, criminal or a person identified as a security risk.

28. The apparatus for identifying the covert foci of attention of the person as in claim 17 wherein the image further comprises a psychiatric chart with a plurality of psychiatric or neurological trigger elements presenting various levels of interest for a psychiatric or neurological patient.

29. The apparatus for identifying the covert foci of attention of the person as in claim 17 wherein the image further comprises a marketing display with a plurality of marketing items presenting various levels of interest for a consumer.

30. The apparatus for identifying the covert foci of attention of the person as in claim 17 further comprising present a plurality of images presented side-by-side.

31. The apparatus for identifying the covert foci of attention of the person as in claim 17 further comprising an eye fixation spot guided across the image where the fixation spot indicates where the person should fixate their gaze where the fixation spot changes either randomly or systematically to obtain a relatively optimal distribution of microsaccades across the image.

32. The apparatus for identifying the covert foci of attention of the person as in claim 30 further comprising a static fixation spot on the images where the static fixation spot indicates where the person should fixate their gaze and where the plurality of images moves randomly or systematically producing a predetermined amount of fixation time on each of the plurality of images.

33. An apparatus for identifying a covert foci of attention of a person comprising:
    a display that presents the person with an image having a plurality of visual elements;
    an eye tracking device that detects trajectories of involuntary eye microsaccades of the subject with respect to the image; and
    a host that associates the eye movements with a visual element of interest within the plurality of elements by extrapolating the trajectories of at least some of the detected eye movements to an area of intersection in the image to determine an area of covert attentional focus.

34. The apparatus for identifying the covert foci of attention of the person as in claim 33 wherein the eye tracking device associating the eye movements with the element further comprises a triangulation processor that triangulates trajectories of the microsaccades to a location of the associated visual element on the image.

35. The apparatus for identifying the covert foci of attention of the person as in claim 33 wherein the means for associating eye movements with the element further comprises an ordering processor associating the eye movements with a plurality of elements of the image and ordering the elements of the image based upon the number of intersecting trajectories of the microsaccades associated with each of the respective visual elements.

36. The apparatus for identifying the covert foci of attention of the person as in claim 33 wherein the means for associating the eye movements with the element further comprises a triangulation processor that triangulating trajectories of the microsaccades to locations on the image and a region of interest processor that increases a weighting of pixels proximate each intersection and decreasing a weighting of pixels relatively far from the intersections.

37. The apparatus for identifying the covert foci of attention of the person as in claim 33 wherein the means for associating the eye movements with the element further comprises triangulation processor that triangulates a set of diverging trajectories of the microsaccades to locations on the image and a region of interest processor increasing a weighting of pixels proximate each intersection and decreasing a weighting of pixels relatively far from the intersections.

38. The method of identifying the covert foci of attention as in claim 1 further comprising measuring voluntary eye movements with respect to the image.

39. The apparatus for identifying the covert foci of attention as in claim 17 further comprising means for measuring voluntary eye movements with respect to the image.

40. The apparatus for identifying the covert foci of attention as in claim 17 further comprising means for measuring a duration of involuntary microsaccadic eye movements of the subject and combining information from the duration measurement with information from the trajectories of the detected eye movements to determine an area of covert attentional focus.

41. The apparatus for identifying the covert foci of attention as in claim 33 further comprising the eye tracking device measuring voluntary eye movements with respect to the image.

42. The apparatus for identifying the covert foci of attention as in claim 33 further comprising the host measuring a duration of microsaccadic eye movements of the subject and combining information from the duration measurement with information from the trajectories of the detected eye movements to determine an area of covert attentional focus.

* * * * *